| United States Patent [19] | [11] 4,010,188 |
| --- | --- |
| Grasselli et al. | [45] Mar. 1, 1977 |

[54] CATALYTIC CONVERSION OF SATURATED HYDROCARBONS TO UNSATURATED PRODUCTS BY OXIDATION IN THE PRESENCE OF A HALOGEN

[75] Inventors: Robert K. Grasselli, Warrensville Heights; Robert C. Miller, Northfield, both of Ohio

[73] Assignee: Standard Oil Company, Cleveland, Ohio

[22] Filed: June 24, 1968

[21] Appl. No.: 739,166

[52] U.S. Cl. .................. 260/465 C; 260/465.3; 260/524 N; 260/533 N; 260/599; 260/604 R
[51] Int. Cl.² .................................. C07C 120/14
[58] Field of Search .................. 260/465.3, 465 C

[56] References Cited

UNITED STATES PATENTS

| 3,152,170 | 10/1964 | Barclay | 260/465.3 |
| 3,338,952 | 8/1967 | Callahan et al. | 260/465.3 |
| 3,365,482 | 1/1968 | Khoobiar | 260/465.3 |
| 3,399,225 | 8/1968 | Tarama et al. | 260/465 |
| 3,424,781 | 1/1969 | Capp et al. | 260/465.3 |
| 3,431,292 | 3/1969 | Callahan et al. | 260/465.3 |

FOREIGN PATENTS OR APPLICATIONS

| 711,964 | 9/1968 | Belgium |
| 6,803,292 | 9/1968 | Netherlands |
| 1,194,855 | 6/1970 | United Kingdom |

*Primary Examiner*—Joseph P. Brust
*Attorney, Agent, or Firm*—Herbert D. Knudsen; Larry W. Evans

[57] ABSTRACT

The instant application is related to a process for the oxidation of saturated hydrocarbons and substituted saturated hydrocarbons in a vapor phase reaction over an antimony-containing oxidation catalyst in which the hydrocarbon in the presence of a minor quantity of an inorganic or organic halide, hydrogen chloride, hydrogen bromide or hydrogen iodide or of a halogen other than fluorine, is reacted with (a) oxygen, to form unsaturated aldehydes and acids or (b) oxygen and ammonia, to form unsaturated nitriles.

9 Claims, No Drawings

CATALYTIC CONVERSION OF SATURATED HYDROCARBONS TO UNSATURATED PRODUCTS BY OXIDATION IN THE PRESENCE OF A HALOGEN

BACKGROUND OF THE INVENTION

Unsaturated aldehydes such as acrolein, methacrolein, cinnamaldehyde and atropaldehyde, unsaturated acids such as acrylic acid, methacrylic acid, cinnamic acid, α-phenyl acrylic acid, and the like are highly desirable compounds having particular use as specialty industrial chemicals and as monomers and comonomers in a variety of commerical polymers. Unsaturated nitriles such as acrylonitrile, methacrylonitrile, cinnamonitrile, atroponitrile and the like are similarly useful chemicals used in the manufacture of fabrics, insecticides, herbicides and plastics. The aforementioned unsaturated compounds are usually manufactured from monoolefinically unsaturated compounds such as propylene, isobutylene isoamylene, α-methyl styrene, β-methyl styrene and the like which are considerably more expensive raw materials than more readily availably saturated and substituted saturated hydrocarbons. To date, commercial manufacture of the desired unsaturated compounds has been most successfully achieved by the vapor phase oxidation or ammoxidation of an olefin or an olefinically unsaturated alkyl aromatic.

Much time has been spent on various methods of converting the cheaper saturated compounds into the desired more valuable unsaturated nitriles, aldehydes and acids in a single step catalytic reaction. Particularly noteworthy is the fact that considerable effort has been expended to effect the desired oxidation of saturated hydrocarbons without breaking off one or more carbon atoms. This effort has met with a conspicuous lack of success and served to focus on the gap in this technology. The instant invention aims to fill that gap.

U.S. Pat. No. 3,365,482 teaches a process for the ammoxidation of saturated hydrocarbons and as background, lists a number of references which teach the ammoxidation of olefinically unsaturated hydrocarbons. Also included is a summary of the difficulties inherent in a process for the ammoxidation of saturated hydrocarbons, which difficulties no one will gainsay.

In U.S. Pat. No. 3,293,290 a process is disclosed for the manufacture of unsaturated aldehydes and acids from either paraffins or monoolefins in which a gaseous mixture of hydrocarbons and oxygen is catalytically converted into the desired products in the presence of hydrogen bromide or hydrogen iodide as a promoter. Table 1 (on page 3, column 5 of '290) indicates that overall percent conversion of propylene feed is about the same whether or not hydrogen bromide is used, and in fact whether or not any promoter is used.

The inappropriateness of hydrogen chloride as a promoter since it gave less unsaturated products than no promoter at all, is emphasized in the very first two tests of '290; to distinguish this reference from the instant invention right at the outset, pertinent figures for conversion of propylene to desired unsaturated products are reproduced from said reference under the heading Desirability of Chloride Promoter in the Examples section of the instant application on pages 10 and 11.

Another halide-promoted catalytic reaction is the subject of U.S. Pat. No. 3,293,292 wherein liquid normal butane is converted to acetic acid in the presence of a cobalt salt which is soluble in the liquid medium in which the oxidation reaction takes place. It will be noted that, unlike the reactions disclosed in U.S. Pat. No. 3,293,290 and the instant invention, the liquid phase reaction involves converting a lower alkane to the saturated acid rather than the unsaturated acids and aldehydes.

In the instant invention, applicants have discovered that saturated hydrocarbons and substituted saturated hydrocarbons having from 3 to 12 carbon atoms per molecule, and preferably from 3 to 9 carbon atoms per molecule, may be readily oxidized or ammoxidized by the instant vapor phase catalytic reaction utilizing an antimony-containing oxidation catalyst provided that a minor quantity of an inorganic or organic halide, a halogen or a halogen acid, as specified hereinafter, is incorporated with the feed. Fluorine and compounds of fluorine are excluded from the scope of the instant invention.

SUMMARY

It is an object of the instant invention to provide a commercial vapor-phase oxidation process for the conversion of inexpensive alkane and aryl-substituted alkane hydrocarbon feedstocks into more valuable unsaturated nitriles, aldehydes and acids.

It is another object of the instant invention to provide a process for the vapor-phase oxidation and ammoxidation of a lower alkane, such as propane, butanes, pentanes, hexanes and aryl substituted alkanes such as n-propyl benzene and cumene to unsaturated nitriles, aldehydes and acids using solid antimony-containing oxidation catalysts in the presence of certain halogens, inorganic halides and lower alkyl halides.

It is a further object of the instant invention to provide a process for the vapor phase catalytic oxidation of an alkane or aryl substituted alkane feed having from 3 to 9 carbon atoms in the presence of halogens other than fluorine, halogen acids other than hydrogen fluorides, lower alkyl halides other than fluorides, and ammonium halides, other than ammonium fluoride, in the vapor state, in conjunction with a molecular oxygen containing gas over an antimony-containing solid oxidation catalyst to form unsaturated nitriles, aldehydes and acids.

DESCRIPTION OF THE PREFERRED EMBODIMENT

It has been found that when small quantities of chlorine, bromine and iodine or certain halides are included in saturated hydrocarbon feed which is passed over the antimony-containing oxidation catalysts disclosed herein, said catalysts show an unexpected and surprisingly high activity toward the otherwise relatively inert paraffinic feed materials. The instant reaction is unique in that the halogen or halide acts as a promoter with known oxidation catalysts.

Compounds which may be oxidized or ammoxidized by the instant process have the structure

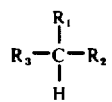

wherein $R_1$, $R_2$ and $R_3$ may be hydrogen, an alkyl or an aryl group, or a substituted alkyl group wherein the substitution is an aryl group, provided said compounds contain at least three carbon atoms. The alkyl groups have from 1 to 8 carbon atoms per molecule (as, for example, methyl, ethyl, isobutyl and hexyl) and preferably from 1 to 4. Most preferred of the aryl groups is the phenyl group. Most preferred reactions are (a) the ammoxidation of propane to acrylonitrile, isobutane to methacrylonitrile, isopropyl benzene to atroponitrile and n-propyl benzene to cinnamonitrile and (b) the oxidation of propane, butane, isobutane, pentane, isopentane, hexane, isohexane, n-propyl benzene and cumene, to form unsaturated aldehydes such as acrolein, methacrolein, crotonaldehyde, γ-ethyl acrolein, β-ethyl crotonaldehyde, 2-hexenal, γ-amylacrolein, cinnamaldehyde and atropaldehyde, and unsaturated acids such as acrylic, vinyl acetic, crotonic, methacrylic, isopropyl acrylic, and cinnamic acid.

The preferred hydrocarbons are the low boiling alkanes having between 3 and 6 carbons. More preferred compounds are propane, isobutane, pentane and isopentane.

Generally, in the production of unsaturated aldehydes by the instant process, some unsaturated acids, olefins and other byproducts of reaction will be formed; in the manufacture of unsaturated nitriles and acids, some unsaturated aldehydes, olefinic and saturated byproducts may also be formed which may be recycled for further conversion to the desired unsaturated acids. When an inorganic halide such as ammonium chloride is used in a process for making predominantly the unsaturated aldehydes and carboxylic acids, some unsaturated nitrile will also be formed due to the liberation of an active nitrogen-containing species in the reaction. Similarly the use of a lower alkyl halide would yield, in addition to the desired unsaturated aldehydes and carboxylic acids, that unsaturated aldehyde or carboxylic acid formed from the alkyl group introduced. Thus propane oxidized in the presence of isobutyl chloride will yield, in addition to acrolein and acrylic acid, some methacrolein and methacrylic acid. It is possible to use aromatic halide compounds in which the alkyl group on the aromatic nucleus conatins a halogen substitution. Such compounds give rise to the formation of unsaturated aldehydes and acids containing the same number of carbon atoms as the halogen-containing compound. Thus isobutane oxidized in the presence of β-chloro-isopropyl benzene will yield in addition to methacrolein and methacrylic acid, some cinnamaldehyde and cinnamic acid. In general, the high cost of halogen-containing alkyl-substituted aromatic compounds will preclude their usage in most applications.

Catalysts that are particularly useful in the instant invention are the unpromoted catalysts disclosed in U.S. Pat. Nos. 3,197,419; 3,198,750; 3,264,225; 3,200,081; 3,152,170; 3,198,751; 3,244,642; 3,258,432 and 3,200,084; and the promoted oxidation catalysts disclosed in U.S. Pat. Nos. 3,328,315; 3,210,295; 3,326,819; 3,338,952 and 3,269,957. It is known that catalysts in the above-identified patents are quite ill-suited to the oxidation of paraffins, being substantially inert, though they are very effective catalysts for the conversions of monoolefins to the corresponding unsaturated aldehydes and acids. It is therefore all the more surprising that these catalysts, which may be prepared by any of the means described in the above-identified patents, and which may be disposed on any suitable catalyst support also as specified in the above-identified issued patents, should exhibit such a surprisingly high activity towards a paraffinic feed as long as the feed included a halogen other than fluorine or a halogen acid other than hydrogen fluoride, or ammonium halide other than ammonium fluoride, or a lower alkyl halide, preferably those having from 3 to 6 carbon atoms. Other inorganic and organic halides may be used but the relatively high cost of said halides is not offset by a superior yield of desirable products. Generally, the halogen or the halogen-containing compound should be added so as to be in the vapor phase in the feed, when the feed is passed over the oxidation catalyst. A relatively small quantity of halogen or halogen-containing compound should be sufficient, generally in a concentration in the range from about 0.001 to about 25 volume percent (calculated as molecular halogen) of the hydrocarbon feed; the more preferred range of halogen in the feed is from about 0.01 to about 10 volume percent (calculated as molecular halogen) of the hydrocarbon feed.

Oxygen for the oxidation reaction may be supplied either as elemental oxygen, air or in any molecular oxygen-containing gas where the components other than oxygen do not interfere with the production of the desired unsaturated oxidation products. In general, from about 0.5 to about 3 moles, but preferably about 1 mole of oxygen per mole of hydrocarbon feed is included in the mixture conducted to the reactors. If desired, oxygen, as also other diluents such as steam and inert gases, may be introduced separately into predetermined parts of the reaction zone.

Ammonia for the conversion of saturated hydrocarbons to unsaturated nitriles may be supplied either as a liquid to the reactor or more preferably, as a preheated gas. In general about 1 mole of ammonia per mole of hydrocarbon feed is included in the mixture conducted to the reactors. Either more or less ammonia may be used, but there is no advantage in using much less or much more than the theoretically indicated amount.

Any reactor, whether fluid-bed or fixed-bed, may be used in the instant process. Reactors suitable for the exothermic process of the instant invention will usually be equipped with heat exchange coils, quenching means, cyclones and the like.

The contact time for the reaction will depend upon various factors, among them the type of catalyst used, its surface area and physical and chemical characteristics, the products desired, whether they be the unsaturated acids or the aldehydes, and the heat of reaction for the particular products desired to be manufactured. In general contact times are short, ranging from about 0.1 to 20 seconds. The contact time, sometimes referred to as the apparent contact time, is determined from the apparent volume of the catalyst and the mass flow of the gases through the reactor.

The temperature is maintained in the reaction zone by pre-heating the feed to a suitable temperature before it enters the reactor. The exothermic heat of oxidation, once the reaction is initiated, will often suffice to maintain the reaction, and excess heat of reaction is removed by the injection of water sprays and by suitable heat transfer devices with which the reactor is equipped.

In general, when operating at pressures near atmospheric, i.e., −10 to 100 psig, temperatures in the range of 500° to 1100° F may be advantageously employed. However, the process may be conducted at other pressures, and in the case where superatmospheric pressures, i.e., above 100 psig are employed somewhat lower temperatures are possible. In the case where this process is employed to convert propane to acrolein, a temperature range of 850° to 1000° F has been found to be optimum at about atmospheric pressure. While pressures other than atmospheric may be employed, it is generally preferred to operate at or near atmospheric pressure, since the reaction proceeds well at such pressures and the use of expensive, high-pressure equipment is avoided.

Reaction products from the reactor emanate as a hot gaseous stream which may be first heat exchanged with incoming feed gases, and then quenched by a suitable liquid, water generally being used. Suitable inhibitors are added to the aqueous solution to prevent polymerization of reaction products and to facilitate their separation and recovery in subsequent operations.

The following examples will serve to illustrate our invention and present typical results which were obtained. All parts referred to are parts by weight, and all ratios are molar ratios, unless otherwise specifically designated.

All conversions are given as Per Pass Percent Conversion and is defined as:

$$\frac{\text{Moles of unsaturated product formed per pass}}{\text{Moles of saturated hydrocarbon fed per pass}} \times 100$$

Desirability of Chloride Promoter: The tests immediately below are reproduced from Table I Colume Column of U.S. Pat. No. 3,293,290.

| Test | 1 | 2 |
|---|---|---|
| Unsaturated Products (percent yields) | | |
| Acrolein | 50 | 40 |
| Acrylic Acid | 11 | 11 |
| Promoter (Vol. %) | None | 0.2 HCl |
| Overall Conversion (%) | 9.7 | 7.6 |

Thus 9.7 mols of 100 mols propylene are converted without a promoter while only 7.6 mols are converted with an HCl promoter. It is apparent that, when one uses the same catalyst, not only is conversion of the feed higher with no promoter at all, but the net make of desirable unsaturated products is also better. Test 1 shows that 100 mols of hydrocarbon (propylene) passed over the unpromoted catalyst result in a net make of 4.85 mols of acrolein and 1.067 mols of acrylic acid; but over the HCl promoted catalyst, Test 2 shows a net make of only 3.04 volumes of acrolein and 0.836 volume of acrylic acid. Clearly hydrogen chloride acts as a retardant or negative promoter.

The patentees in the above-identified reference '290 have discovered that a mixture of ferric and bismuth phosphomolybdates is a "highly active catalyst which shows an enhanced activity for alkane oxidation in the presence of bromine compounds" (Column 2, lines 33–35) as exemplified by the experimental results tabulated in Table 2, page 3, of their specification. The pertinent details of five tests tabulated in Table 2, using hydrogen bromide as promoter, are reproduced below.

| Test | 6 | 8 | 10 | 12 | 13 | 14 |
|---|---|---|---|---|---|---|
| Unsaturated Products (percent yields) | | | | | | |
| Acrolein | 20 | 13 | 11 | 14 | 15 | 18 |
| Acrylic Acid | 31 | 12 | 16 | 28 | 18 | 24 |
| Overall Conversion (%) | 11.1 | 8.0 | 7.3 | 13.5 | 8.7 | 11.9 |
| Acrolein, Net Make (%)* | 2.22 | 1.04 | 0.803 | 1.89 | 1.31 | 2.14 |
| Acrylic Acid, Net Make (%)* | 3.44 | 0.96 | 1.17 | 3.78 | 1.57 | 2.86 |

*calculated

Clearly these data would suggest that halide promotion of oxidation catalysts, particularly of the iron and bismuth salts of phosphomolybdic acid is of little more than academic curiosity.

EXAMPLE I

Quartz (C.P.) was crushed and screened; the particles within the range from 20–35 mesh (Tyler Screens) were loaded into a reactor of approximately 100 ml. capacity. When the reactor attained the desired temperature, the gas feed was metered into it by Rotameters, the individual components of the gaseous feed being mixed in a manifold immediately prior to entering the reactor. A run without the halide promoter preceded one using the halide promoter which was introduced into the manifold in a gaseous state. Water was usually added to the feed as liquid, to facilitate temperature control, by a Sigmamotor pump through capillary tubing which could be preheated if desired, prior to entering the manifold.

TABLE I

| Material in Reactor | Halide Promotion | Reactor Temp. °C. | Feed i-C₄/air/H₂O/HCl | Contact Time (secs.) | Per Pass Percent Conversion to | |
|---|---|---|---|---|---|---|
| | | | | | Olefins | Aldehydes |
| Crushed quartz | none | 600 | 1/11/5/0 | 3.5 | 6.0 | 1.6 |
| " | HCl | 600 | 1/11/5/0.25 | 3.5 | 40.6 | 6.4 |

EXAMPLES 2–4

An antimony-uranium catalyst was prepared as described in Example 1 of U.S. Pat. No. 3,341,471. The heat-treated catalyst was loaded into a reactor with about 100 ml. catalyst capacity. The components of the gas feed were metered by Rotameters and mixed in a manifold immediately prior to entering the reactor when the desired reactor temperature was attained. A mixture of iso-butane, ammonia, air, oxygen and water in the volumetric ratios indicated hereinbelow in Table II, was fed to the reactor and the effluent analyzed for the reaction products. Water was added to the feed as liquid to facilitate temperature control, as in the previous Example 1. Subsequently a run was made under identical conditions, except that HCl was added as a promoter.

below in Table III was fed to the reactor and the effluent analyzed for the reaction products. Water was added to the feed as liquid to facilitate temperature control, as in the previous Example 1. In some examples the hydrocarbon feed was passed over the catalyst, first, without any halogen or halide promoter and the reaction products were analyzed. Immediately thereafter a run was made under identical conditions, except that a halide promoter (hydrogen chloride gas) was used.

Successive examples were run with other catalysts in a manner similar to that described above. Each catalyst used is identified hereinbelow with an alphabetical code corresponding to footnotes that refer to the details of their preparation as found in specific references. All catalysts were supported on silica.

TABLE II

| Example | Catalyst in Reactor | Feed Ratio i-$C_4$/$NH_3$/Air/$O_2$/$H_2O$/HCl | Reactor Temp. °C. | Contact Time (secs.) | Per Pass Percent Conversion to methacrylonitrile | Per Pass Percent Conversion to Acrylonitrile |
|---|---|---|---|---|---|---|
| 2 | $USb_{4.6}O_{13.2}$ | 1/1.5/10/1/5/0 | 550 | 3.2 | 3.9 | 2.9 |
| 3 | " | 1/1.5/10/1/5/0.25 | 525 | 3.3 | 11.3 | 8.2 |
| 4 | " | 1/1.5/10/1/5/0.25 | 550 | 3.2 | 10.0 | 14.5 |

*supported on silica

EXAMPLES 5–14

An antimony-iron catalyst was prepared as described in Example 2 of U.S. Pat. No. 3,341,471. The heat-treated catalyst was loaded into a reactor with about 100 ml. catalyst capacity. The components of the gas feed were metered by Rotameters and mixed in a manifold immediately prior to entering the reactor when the desired reactor temperature was attained. A hydrocarbon mixture in the volumetric ratios indicated herein-

TABLE III

| Example | Catalyst in Reactor | Feed Ratio i-$C_4$/$NH_3$/Air/$O_2$/$H_2O$/HCl | Reactor Temp. °C. | Contact Time (secs.) | Per Pass Percent Conversion to Methacrylonitrile | Per Pass Percent Conversion to Acrylonitrile |
|---|---|---|---|---|---|---|
| 5 | Antimony-[a] iron oxides | 1/2/11/0/5/0 | 600 | 3.15 | | [e] |
| | " | 1/2/11/0/5/0.25 | 600 | 3.15 | 13.5 | 1.6 |
| 6 | Antimony-[b] Thorium oxides | 1/1.5/11/0/5/0.25 | 550 | 3.5 | 16.7 | 14.3 |
| 7 | Antimony-[c] manganese oxides | 1/1.5/11/0/5/0.25 | 550 | 3.5 | 15.9 | 11.2 |
| 8 | Antimony-[d] tin oxides | 1/1.5/11/0/5/0.25 | 550 | 3.5 | 20.3 | 12.2 |
| 9 | Iron-promoted[e] antimony-uranium oxides $Fe_{.1}USb_{4.6}O_{13.3}$ | 1/1.5/10/1/5/0 | 520 | 4.0 | 1.8 | 0 |
| | " | 1/1.5/10/1/5/0.25 | 520 | 4.0 | 35.9 | 18.8 |
| 10 | Copper-promoted[f] antimony-uranium oxides $Cu_{.3}USb_{4.6}O_{13.4}$ | 1/1.5/10/1/5/0.25 | 540 | 3.9 | 14.1 | 13.6 |
| 11 | Copper and bismuth[g] promoted antimony-uranium oxides $Cu_{.15}Bi_{.15}USb_{4.6}O_{13.7}$ | 1/1.5/10/1/5/0.25 | 520 | 3.95 | 17.3 | 13.3 |
| 12 | Cobalt-promoted[h] antimony-uranium oxides $Co_{.1}USb_{4.6}O_{13.5}$ | 1/1.5/10/1/5/0.25 | 540 | 3.90 | 15.4 | 9.7 |
| 13 | Nickel-promoted[i] antimony-uranium oxides $Ni_{.5}USb_{4.6}O_{13.8}$ | 1/1.5/10/1/5/0.25 | 560 | 3.85 | 11.3 | 13.0 |
| 14 | Magnesium-promoted[j] antimony-uranium oxides $Mg_{.2}USb_{4.6}O_{13.6}$ | 1/1.5/10/1/5/0.25 | 560 | 3.9 | 12.5 | 10.6 |

[a,b,c,d]See U.S. Pat. No. 3,341,471
[e,f,g,h,i,j]See U.S. Pat. No. 3,328,315

The antimony-containing catalysts described above gave comparable results with hydrogen bromide and iodide; ammonium halides and lower alkyl halogen-substituted hydrocarbons disclosed herein were also effective promoters.

Other antimony-containing catalysts which contained bismuth, platinum, boron, silver, cobalt, nickel, lead, arsenic, tungsten, phosphorus, aluminum, calcium and caesium gave similar results when a saturated hydrocarbon was ammoxidized in the presence of hydrogen chloride, bromide or iodide; chlorine, bromine or iodine; ammonium chloride, bromide or iodide; and lower alkyl halides containing from 3 to 6 carbon atoms.

EXAMPLES 15–23

The runs set forth in Table IV hereinbelow were performed in a manner similar to those set forth in Table III above, except that no ammonia was introduced into the reactor. Thus the unsaturated aldehydes and acids were formed. In the examples immediately following, only the amount of unsaturated aldehydes formed are shown as the unsaturated carboxylic acids formed were minor quantities, the conditions of reaction having been adjusted to favor the formation of the unsaturated aldehydes. All catalysts were supported on silica and prepared as before.

cium and caesium gave similar results when a saturated hydrocarbon was oxidized in the presence of hydrogen chloride, bromide or iodide; chlorine, bromine or iodine; ammonium chloride, bromide or iodide; and lower alkyl halides containing from 3 to 6 carbon atoms.

EXAMPLES 24–26

The following runs were made using a copper and magnesium promoted antimony-uranium catalyst, prepared as disclosed in U.S. Pat. No. 3,328,315, to demonstrate that with certain catalysts, increased reactor temperatures, with a halide promoter, will give increased conversions of the saturated hydrocarbon to desired unsaturated nitriles.

TABLE V

Catalyst in reactor: $Cu_{.15}Mg_{.15}USb_{4.6}O_{13.6}$
Feed Ratio (i-$C_4$/$NH_3$/Air/$O_2$/$H_2O$/HCl): 1/1.5/10/1/5/0.25

| Example | Reactor Temp. °C. | Contact Time (secs.) | Per Pass Percent Conversion to | | |
|---|---|---|---|---|---|
| | | | Methacrylo-nitrile | Acrylo-nitrile | Combined unsaturated nitriles |
| 24 | 500 | 4.0 | 5.3 | 2.0 | 7.3 |
| 25 | 540 | 3.9 | 17.4 | 10.5 | 27.9 |
| 26 | 560 | 3.85 | 17.1 | 15.7 | 32.8 |

EXAMPLES 27–28

Halide promotion of certain promoted antimony-containing oxidation catalysts exhibits a peculiar sensitivity to temperature, in that a relatively small change

TABLE IV

| Example | Catalyst in Reactor | Feed Ratio | Reactor Temp. °C. | Contact Time (secs.) | Per Pass Percent Conversion to | |
|---|---|---|---|---|---|---|
| | | | | | Meth-acrolein | Acrolein |
| 15 | Uranium-antimony oxides $USb_{4.6}O_{13.2}$ | i-$C_4$/Air/$O_2$/$H_2O$/HCl 1/8.5/2.5/5/0 | 550 | 3.2 | 0.3 | 0.6 |
| 16 | " | 1/8.5/2.5/5/0.25 | 550 | 3.2 | 17.2 | 23.1 |
| 17 | Iron-antimony oxides $FeSb_{8.7}O_{18.7}$ | 1/11/0/5/0.25 | 500 | 3.4 | 16.4 | 5.4 |
| 18 | Antimony-thorium oxides | 1/11/0/5/0.25 | 550 | 3.2 | 11.1 | 9.3 |
| 19 | Antimony-manganese oxides | 1/11/0/5/0.25 | 500 | 3.4 | 21.0 | 11.6 |
| 20 | Antimony-tin oxides | 1/11/0/5/0.25 | 500 | 3.4 | 19.8 | 8.7 |
| 21 | Iron-promoted antimony-uranium oxides $Fe_{.1}USb_{4.6}O_{13.3}$ | 1/11/0/5/0.25 | 500 | 3.4 | 31.2 | 15.3 |
| 22 | $Fe_{.1}USb_{4.6}O_{13.3}$ " | $C_3$/Air/$O_2$/$H_2O$/HCl 1/10/1/5/0.25 | 500 | 3.4 | — | 20.9 |
| 23 | $Fe_{.1}USb_{4.6}O_{13.3}$ " | $C_3$/Air/$O_2$/$H_2O$/Hbr 1/10/1/5/0.25 | 470 | 3.5 | — | 29.8 |

Other antimony-containing catalysts which contained bismuth, platinum, boron, silver, cobalt, nickel, lead, arsenic, tungsten, phosphorus, aluminum, calcium and caesium gave similar results when a saturated hydrocarbon was ammoxidized in the presence of hydrogen chloride, bromide or iodide; chlorine, bromine or iodine; ammonium chloride, bromide or iodide; and lower alkyl halides containing from 3 to 6 carbon atoms.

of reactor temperature coupled with a change in the ratio of the feed components can form more of one product (methacrylonitrile, say) and less of another (acrylonitrile, say) or vice versa.

TABLE VI

Catalyst in Reactor: $Zn_{.3}USb_{4.6}O_{13.6}$

| Example | Feed Ratio i-$C_4$/$NH_3$/Air/$O_2$/$H_2O$/HCl | Reactor Temp. °C. | Contact Time (secs.) | Per Pass Percent Conversion to | |
|---|---|---|---|---|---|
| | | | | Methacrylo-nitrile | Acrylo-nitrile |
| 27 | 1/1.5/10/1/5/0.25 | 500 | 4.0 | 21.2 | 10.5 |

TABLE VI-continued

Catalyst in Reactor: $Zn_.3USb_{4.6}O_{13.8}$

| Example | Feed Ratio i-$C_4$/$NH_3$/Air/$O_2$/$H_2O$/HCl | Reactor Temp. °C. | Contact Time (secs.) | Per Pass Percent Conversion to | |
|---|---|---|---|---|---|
| | | | | Methacrylonitrile | Acrylonitrile |
| 28 | 1/3/20/2/10/0.5 | 540 | 3.9 | 16.3 | 20.6 |

EXAMPLES 29–32

Antimony-containing oxidation catalysts were used for the ammoxidation of saturated hydrocarbons other than iso-butane. The procedure for carrying out these runs was similar to that described in Examples 3–8 hereinabove. Some of the hydrocarbon feeds ammoxidized over particular catalysts gave unsaturated nitrile products described in the table immediately hereinbelow.

TABLE VII

| Example | Catalyst in Reactor | Feed Components-Ratio in Feed | Reactor Temp. °C. | Contact Time (secs.) | Per Pass Percent Conversion to Unsaturated nitriles |
|---|---|---|---|---|---|
| 29 | Iron-promoted antimony-uranium oxides $Fe_.1USb_{4.6}O_{13.6}$ | $C_3$/$NH_3$/Air/$O_2$/$H_2O$/HCl 1/1.5/10/1/5/0.25 | 500 | 3.85 | Acrylonitrile 25.8 |
| 30 | Antimony-iron oxides $FeSb_{n.67}O_{18.6}$ | 1/1.5/10/1/5/0.25 | 500 | 3.15 | 11.3 |
| 31 | Iron-promoted antimony-uranium oxides $Fe_.1USb_{4.6}O_{13.4}$ | n-propylbenzene/$NH_3$ Air/$O_2$/$H_2O$/HCl | 480 | 2.0 | Cinnamonitrile 28.7 |
| 32 | as above | cumene/$NH_3$/Air/$O_2$/$H_2O$/HCl | 480 | 2.0 | Atroponitrile 37.9 |

EXAMPLE 33

The examples hereinbelow demonstrate that various inorganic halides, certain organic halides, particularly the lower alkyl halides having from 2 to 5 carbon atoms, in addition to the halogens and the halogen acids, except that the halogen should not be fluorine, may be used in the instant invention.

In general, the use of bromides and iodides will permit the use of lower reaction temperatures and contact times.

TABLE VIII

Catalyst in Reactor: Iron-promoted antimony-uranium oxides $Fe_.1USb_{4.6}O_{13.4}$

| Example | Feed Components-Ratio in Feed | Reactor Temp. °C. | Contact Time (secs.) | Per Pass Percent Conversion to | |
|---|---|---|---|---|---|
| | | | | Methacrylonitrile | Acrylonitrile |
| 33 | i-$C_4$/$NH_3$/Air/$O_2$/$H_2O$/HBr 1/1.5/10/1/5/0.25 | 450 | 4.5 | 38.8 | 5.1 |
| 34 | i-$C_4$/$NH_3$/Air/$O_2$/$H_2O$/HI 1/1.5/10/1/5/0.25 | 510 | 4.1 | 40.3 | 4.4 |
| 35 | i-$C_4$/$NH_3$/Air/$O_2$/$H_2O$/$NH_4Cl$ 1/1.5/10/1/5/0.25 | 540 | 4.0 | 25.7 | 8.8 |
| 36 | i-$C_4$/$NH_3$/Air/$O_2$/$H_2O$/n-propyl 1/1.5/10/1/5/0.25 bromide | 450 | 4.5 | 32.3 | 21.7 |
| 37 | $C_3$/$NH_3$/Air/$O_2$/$H_2O$/ethyl 1/1.5/10/1/5/0.25 chloride | 500 | 4.0 | — | 22.6 |
| 38 | $C_3$/$NH_3$/Air/$O_2$/$H_2O$/HBr 1/1.5/10/1/5/0.25 | 490 | 4.0 | — | 35.7 |

We claim:

1. A process for the production of acrylonitrile or methacrylonitrile wherein a hydrocarbon consisting essentially of propane or isobutane is reacted with ammonia and a molecular oxygen containing gas, at a temperature of 250° C to 800° C, in the presence of an ammoxidation catalyst and a minor quantity of a halogen containing component wherein said ammoxidation catalyst is antimony oxide in combination with at least one other metal oxide selected from the group consisting of tin oxide, uranium oxide or manganese oxide and wherein said halogen component consists essentially of at least one of $Cl_2$, $Br_2$, $I_2$, HCl, HBr, HI, $NH_4Cl$, $NH_4Br$, $NH_4I$, a lower alkyl chloride, a lower alkyl bromide or a lower alkyl iodide.

2. A process for the preparation of a monoolefinically unsaturated nitrile consisting essentially of reacting a saturated hydrocarbon selected from the group consisting of propane which produces acrylonitrile, isobutane which produces acrylonitrile or methacrylonitrile or mixtures of acrylonitrile and methacrylonitrile, n-propyl benzene which produces cinnamonitrile, and cumene which produces atroponitrile, with a molecular oxygen-containing gas and ammonia in the presence of from about 0.001 to about 25 volume percent calculated as molecular halogen based on the saturated hydrocarbon, of a halogen or a halogen-substituted compound selected from the group consisting of chlorine, bromine and iodine, a halogen acid selected from the group consisting of hydrogen chloride, hydrogen bromide and hydrogen iodide, a lower alkyl chloride, bromide or iodide, and an ammonium halide selected from the group consisting of ammonium chloride, ammonium bromide and ammonium iodide, over a catalyst consisting essentially of antimony oxide in combination with at least one other polyvalent metal oxide selected from the group consisting of uranium, iron, thorium, manganese and tin, and optionally at least one other polyvalent metal oxide selected from the group consisting of copper, bismuth, nickel, cobalt, magnesium and zinc, said antimony being present on a molar basis as the major metal component, in a pressure range of from about 7 pounds per square inch absolute to about 300 pounds per square inch absolute, at a temperature in the range of from about 250° C to about 800° C, and recovering the monoolefinically unsaturated nitriles formed.

3. The process in claim 2 wherein the catalyst consists of the oxides of antimony and uranium.

4. The process in claim 2 wherein the catalyst consists of the oxides of antimony and iron.

5. The process in claim 2 wherein the catalyst consists of the oxides of antimony, uranium and iron.

6. The process of claim 5 wherein the ammonium halide is ammonium chloride, the halogen acid is hydrogen chloride, and the lower alkyl halide is an alkyl chloride containing from 3 to 6 carbon atoms.

7. The process of claim 6 wherein the amount of said halogen or the amount of molecular halogen in said halogen-substituted compound is present in the range from 0.05 to 15 mole percent of the saturated hydrocarbon introduced into the reaction zone.

8. The process of claim 7 wherein said molecular oxygen-containing gas is air.

9. The process of claim 8 wherein the molar ratio of said saturated hydrocarbon to air is in the range from 1:5 to 1:200 and the molar ratio of saturated hydrocarbon to ammonia is in the range of 1:0.1 to 1:5.

* * * * *